United States Patent
Sbodio et al.

(10) Patent No.: US 11,619,918 B2
(45) Date of Patent: Apr. 4, 2023

(54) DETERMINING AMBIENT CONTROLS

(71) Applicant: International Business Machines Corporation, Armonk, NY (US)

(72) Inventors: Marco Luca Sbodio, Dublin (IE); Caroline A. O'Connor, Kilkenny (IE); Omar O'Sullivan, Delgany (IE); Seshu Tirupathi, Dublin (IE)

(73) Assignee: International Business Machines Corporation, Armonk, NY (US)

( * ) Notice: Subject to any disclaimer, the term of this patent is extended or adjusted under 35 U.S.C. 154(b) by 106 days.

(21) Appl. No.: 17/034,037

(22) Filed: Sep. 28, 2020

(65) Prior Publication Data

US 2022/0100157 A1 Mar. 31, 2022

(51) Int. Cl.
G05B 19/042 (2006.01)
G06N 20/00 (2019.01)

(52) U.S. Cl.
CPC .......... *G05B 19/042* (2013.01); *G06N 20/00* (2019.01); *G05B 2219/25011* (2013.01); *G05B 2219/2614* (2013.01)

(58) Field of Classification Search
CPC ........ G05B 19/042; G05B 2219/25011; G05B 2219/2614; G06N 20/00
See application file for complete search history.

(56) References Cited

U.S. PATENT DOCUMENTS

| | | | |
|---|---|---|---|
| 5,197,941 A | 3/1993 | Whitaker | |
| 6,536,675 B1 | 3/2003 | Pesko et al. | |
| 2005/0015122 A1* | 1/2005 | Mott | A61M 21/00 607/88 |
| 2017/0245354 A1* | 8/2017 | Yadav | H05B 47/19 |
| 2018/0043130 A1* | 2/2018 | Moore-Ede | A61M 21/02 |
| 2018/0318602 A1* | 11/2018 | Ciccarelli | A61M 21/02 |
| 2019/0209806 A1 | 7/2019 | Allen et al. | |
| 2020/0208469 A1* | 7/2020 | Hebeisen | H05B 45/20 |

(Continued)

FOREIGN PATENT DOCUMENTS

| | | |
|---|---|---|
| CN | 104685428 A | 6/2015 |
| KR | 101851690 B1 | 4/2018 |

(Continued)

OTHER PUBLICATIONS

Wikipedia, "Building automation", From Wikipedia, the free encyclopedia, last edited on Jun. 5, 2020, 8 pages.

(Continued)

*Primary Examiner* — Chad G Erdman
(74) *Attorney, Agent, or Firm* — Donald J. O'Brien

(57) ABSTRACT

Embodiments are disclosed for a method. The method includes generating statistical models of circadian rhythms based on circadian rhythm data generated by mobile computing devices of occupants of a building having a building automation system. The method also includes identifying room occupants of a room disposed within the building. Additionally, the method includes determining ambient settings for an ambient system operated by the building automation system based on a subset of the statistical models, wherein the subset corresponds to the identified room occupants. The method further includes determining a trade-off ambient setting based on the ambient settings.

14 Claims, 6 Drawing Sheets

(56) References Cited

U.S. PATENT DOCUMENTS

2021/0128942 A1* 5/2021 Pederson ............. A61B 5/0002
2021/0290973 A1* 9/2021 Moore-Ede ........... A61M 21/00

FOREIGN PATENT DOCUMENTS

WO        2015184019 A1    12/2015
WO        2019119231 A1     6/2019

OTHER PUBLICATIONS

Unknown, "Circadian Rhythms", National Institute of General Medical Sciences, printed Jun. 11, 2020, 3 pages.

Unknown, "Oura Ring", printed Jun. 11, 2020, 11 pages <https://ouraring.com/how-oura-works/>.

Konis, K., "A Novel Circadian Daylight Metric for Building Design and Evaluation", Building and Environment, Nov. 2016, 38 pages.

Anonymous, "Method of Customized Personal Lighting Adjustment for Maintain Body's Natural Rhythms and Health Lifestyle", An IP.com Prior Art Database Technical Disclosure, IP.com No. IPCOM000248234D, IP.com Electronic Publication Date: Nov. 10, 2016, 15 pages.

Mell et al., "The NIST Definition of Cloud Computing", Recommendations of the National Institute of Standards and Technology, Sep. 2011, 7 pages.

* cited by examiner

DETERMINING AMBIENT CONTROLS

BACKGROUND

The present disclosure relates to ambient controls, and more specifically, to determining ambient controls.

Building automation is the automatic centralized control of a building's ambient controls. Ambient controls can include the heating, ventilation, air conditioning, lighting, and the like, which may be operated by a building management system, also referred to herein as a building automation system (BAS). In this way, a BAS can improve occupant comfort, efficiently operate building systems, reduce energy consumption and operating costs, and improve the life cycle of utilities.

SUMMARY

Embodiments are disclosed for a method. The method includes generating statistical models of circadian rhythms based on circadian rhythm data generated by mobile computing devices of occupants of a building having a building automation system. The method also includes identifying room occupants of a room disposed within the building. Additionally, the method includes determining ambient settings for an ambient system operated by the building automation system based on a subset of the statistical models, wherein the subset corresponds to the identified room occupants. The method further includes determining a trade-off ambient setting based on the ambient settings.

Further aspects of the present disclosure are directed toward systems and computer program products with functionality similar to the functionality discussed above regarding the computer-implemented methods. The present summary is not intended to illustrate each aspect of, every implementation of, and/or every embodiment of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
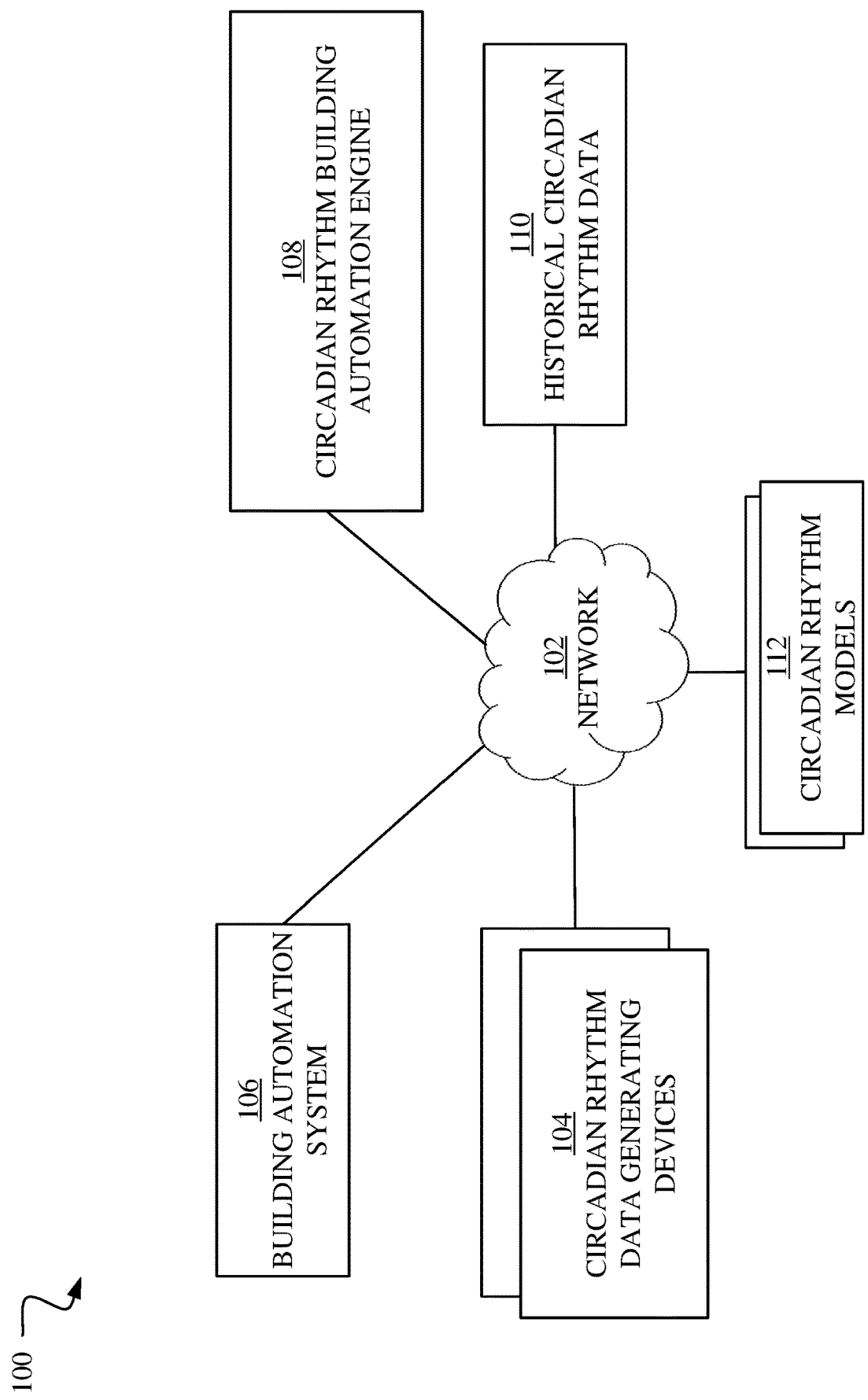
FIG. 1 is a block diagram of an example system for determining ambient settings, in accordance with some embodiments of the present disclosure.

While the present disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the spirit and scope of the present disclosure.

DETAILED DESCRIPTION

As stated previously, building automation systems can improve occupant comfort, efficiently operate environmental and lighting systems, reduce energy consumption and operating costs, and improve the life cycle of environmental and lighting equipment. Further, the advent of the Internet of Things (IoT) technology can make buildings, "smart." Accordingly, building automation systems can use real time information from IoT sensors in the building (and models built with historical data) to control the ambient features (heating, ventilation, lighting, and the like). Additionally, a BAS may also use profiles and/or the predetermined preferences of a smart building's occupants to control the systems under building automation. However, even personal profiles and preferences may not account for the changes in the occupants' physical comfort throughout the day.

A person's physical comfort can be related to biological cycles that are omnipresent in the mammalian nervous system. The frequencies of these cycles, also referred to herein as rhythms, can range from 100 cycles per second (100 Hertz) to just once per year (or 0.00000003 Hz). Biological rhythms are generally classified into three major categories according to their period: ultradian, infradian, and circadian. Ultradian rhythms have a period of less than 24 hours, e.g. the alternation of deep sleep and rapid eye movement (REM) sleep in human beings, which occurs about once every 90 minutes when someone is asleep. Infradian rhythms have a period of more than 24 hours, e.g., the hibernation cycle in bears. Circadian rhythms have a period of approximately 24 hours, e.g. the sleep-wake cycle, the body-temperature cycle, the cycles in which a number of hormones are secreted, and the like.

Accordingly, embodiments of the present disclosure can incorporate circadian rhythm data in the models used to control environmental systems under building automation. More specifically, a BAS can use the circadian rhythm of the occupants of a building to make determinations about the operation of the ambient systems that the BAS controls. Advantageously, using circadian rhythm data in this way can tailor the ambience features of each room in a building to the occupants' comfort. In this way, embodiments of the present disclosure can affect the circadian rhythms of the building's occupants, and therefore improve their well-being. Further, improving the occupants' well-being in this way can improve their productivity.

FIG. 1 is a block diagram of an example system 100 for determining ambient controls in the rooms of a building, in accordance with some embodiments of the present disclosure. The system 100 includes a network 102, circadian rhythm data generating devices 104, building automation system (BAS) 106, circadian rhythm building automation engine 108, and historical circadian rhythm data 110, and circadian rhythm models 112. The network 102 may be a local area network, wide area network, or collection of computer communication networks that facilitates communication between components of the system 100, specifically, between the circadian rhythm data generating devices 104, BAS 106, circadian rhythm building automation engine 108, historical circadian rhythm data 110, and circadian rhythm models 112. In some embodiments, the network 102 can be the Internet.

The circadian rhythm data generating devices 104 can be mobile computing devices, such as smart phones, smart watches, smart jewelry, and the like, that are carried and/or worn by the occupants of a room in a building, and generate circadian rhythm data. The circadian rhythm data can include biological and/or other information relevant to the circadian rhythm of the room occupant carrying and/or wearing the circadian rhythm data generating device 104. In some embodiments of the present disclosure, the circadian rhythm data generating device 104 can include one or more sensors to capture biological measurements, such as, an infrared light emitting diode (LED), negative temperature coefficient (NTC) temperature sensor, accelerometer, gyroscope, and the like. These sensors can capture body measurements, such as, pulse, heart rate variability (HRV), blood pressure, oxygen levels, temperature, and the like. Additionally, the circadian rhythm data generating device 104 can capture the occupants' movement, steps, active and inactive periods of time, and the like.

The building automation system 106 can be an automated and centralized control for operating a building's ambient systems. The ambient systems can include the heating, air conditioning, ventilation, lighting, and the like, for the rooms and corridors of the building.

The circadian rhythm building automation engine 108 can analyze the data from the circadian rhythm data generating devices 104 in real time, and use pre-built statistical models to determine values for the ambient settings of the building automation system 106. According to some embodiments of the present disclosure, the circadian rhythm building automation engine 108 can use current and forecast circadian rhythm data of a room's occupants to determine the ambience classifications of the room.

Additionally, in some embodiments of the present disclosure, the circadian rhythm building automation engine 108 can identify another room (or part of a room) in the building that meets the ambience classifications for the room's occupants. In such embodiments, the circadian building automation engine 108 can provide a notification to one of the room occupants indicating the identified room (or part thereof). Further, in some embodiments of the present disclosure, the circadian rhythm building automation engine 108 can direct the building automation system 106 to set the ambience features of the room to achieve the identified ambience classification for the occupants.

When the room is occupied by more than one occupant, the circadian rhythm building automation engine 108 can determine ambient settings of the building automation system 106 that represent a trade-off between the various settings that may be appropriate for each individual occupant. For example, if an appropriate temperature for a first occupant is 72 degrees Fahrenheit, and 74 degrees for a second occupant, the circadian rhythm building automation engine 108 can set the temperature for the heating (or cooling) system to an average temperature, e.g., 73 degrees. In some embodiments of the present disclosure, the circadian rhythm building automation engine 108 can use the circadian rhythm models 112 to determine ambient settings for each occupant and calculate a trade off based on multiple determined ambient settings. More specifically, the circadian rhythm models 112 can use individual machine learning algorithms for each occupant, wherein occupants with similar circadian rhythm data patterns can be grouped and the ambient settings determined accordingly. Alternatively, the circadian rhythm building automation engine 108 can use the circadian rhythm models 112 to determine the ambient setting based on circadian rhythm data for multiple occupants. In this way, the circadian rhythm building automation engine 108 can determine an ambient setting corresponds to the circadian rhythm data of a group of occupants.

More specifically, the circadian rhythm building automation engine 108 can compile historical circadian rhythm data 110 from the circadian rhythm data generating devices 104 in a datastore. Additionally, the circadian rhythm building automation engine 108 can generate statistical models and machine learning models from the historical circadian rhythm data 110, such as circadian rhythm models 112.

Further, the circadian rhythm building automation engine 108 can accumulate the historical circadian rhythm data 110 into historical time series, which can be used to build statistical models. A statistical model is a mathematical model that uses statistical assumptions to generate sample data. In this way, the statistical models can represent projections of circadian rhythm cycles for individual occupants based on historical data. Accordingly, the circadian rhythm building automation engine 108 can determine ambient settings for the building automation system 106 based on the statistical models. Further, the circadian rhythm building automation engine 108 can determine the ambient settings before the occupants enter the room, and direct the building automation system 106 to adjust the ambient settings accordingly.

According to some embodiments of the present disclosure, the circadian rhythm building automation engine 108 can use machine learning to determine the ambient settings for the building automation system 106. Machine learning is a process wherein a computer algorithm is trained to make a specific classification. For example, machine learning algorithms (learners) can be trained to identify classes of objects in a digital photograph, predict a future shopping choice of a potential customer in a marketing database, and the like. Accordingly, the circadian rhythm data engine 108 can train the circadian rhythm models 112 to determine ambience classifications based on the historical circadian rhythm data 110 and/or statistical models for a room occupant. The ambience classifications can indicate specific settings for heating, air conditioning, ventilation, lighting, and the like. For example, the circadian rhythm data building automation engine 108 can train machine learning models to select a heating or cooling setting based on the body temperature of the occupants of the room, the number of people in the room, current room temperature, and/or the pulse rate of the occupants.

Figure 2:
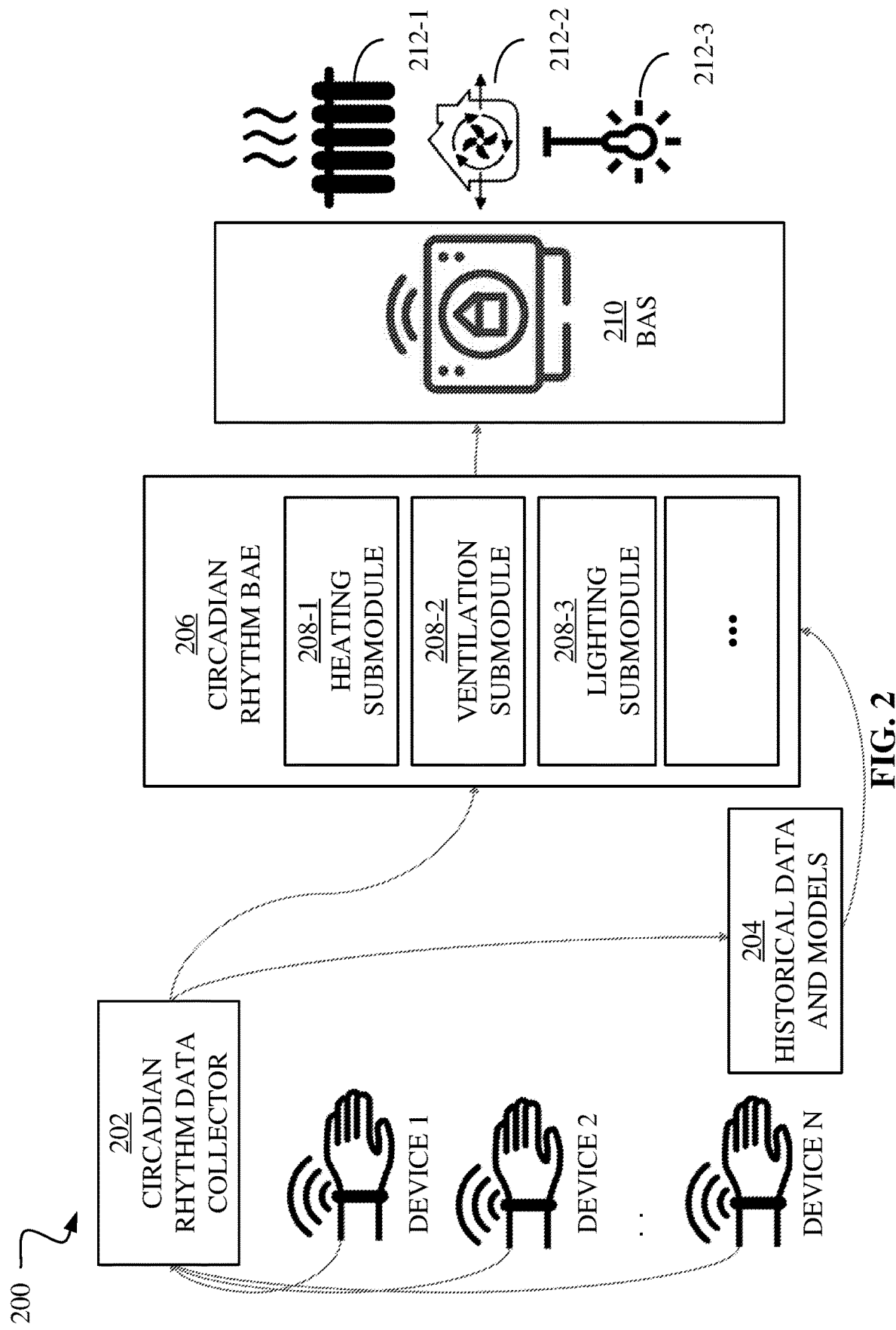
FIG. 2 is a block diagram of an example system for determining ambient settings, in accordance with some embodiments of the present disclosure.

FIG. 2 is a block diagram of an example process 200 for determining ambient controls, in accordance with some embodiments of the present disclosure. This process 200 can include devices 1 through n, circadian rhythm data collector 202, historical data and models 204, circadian rhythm building automation engine (BAE) 206, building automation system 210, and ambient systems 212. The devices 1 through n can be similar to the circadian rhythm data generating devices 104 described with respect to FIG. 1. In this example, the devices 1 through n may be smart watches worn by n occupants of a room. The historical data and models 204 can represent a combination of the historical circadian rhythm data 110 and circadian rhythm models 112. The circadian rhythm building automation engine 206 can be similar to the circadian rhythm building automation engine 108. The building automation system 210 can be similar to the building automation engine 106.

In the process 200, the circadian rhythm data collector 202 can collect circadian rhythm data from the devices 1 through n and store this data in the historical data and models 204. Further, the circadian rhythm data collector 202 can train the models of the historical data and models 204 based on the collected historical data.

According to some embodiments of the present disclosure, the circadian rhythm building automation engine 206 can include submodules for each of the ambient systems 212 under the control of the building automation system 210. In this example, the ambient systems 212 include a heating system 212-1, ventilation system 212-2, and lighting system 212-3. Accordingly, the circadian rhythm building automation engine 206 includes heating submodule 208-1, ventilation submodule 208-2, and lighting submodule 208-3. Further, the circadian rhythm building automation engine 206 can include additional submodules for additional ambient systems, such as cooling systems and so on. According to some embodiments of the present disclosure, the heating submodule 208-1 can determine the corresponding heat setting for a room based on the historical data and models 204 for the room occupants wearing devices 1 through n. Similarly, the ventilation submodule 208-2 can determine the corresponding ventilation setting for the room based on the historical data and models 204 for the room occupants wearing devices 1 through n. Additionally, the lighting submodule 208-3 can determine the corresponding lighting for the room based on the historical data and models 204 for the room occupants wearing devices 1 through n.

Accordingly, the circadian rhythm building automation engine 206 can provide the ambient settings for the building automation system 210. Additionally, the building automation system 210 can direct the ambient systems 212 to operate based on the determined settings.

Figure 3:
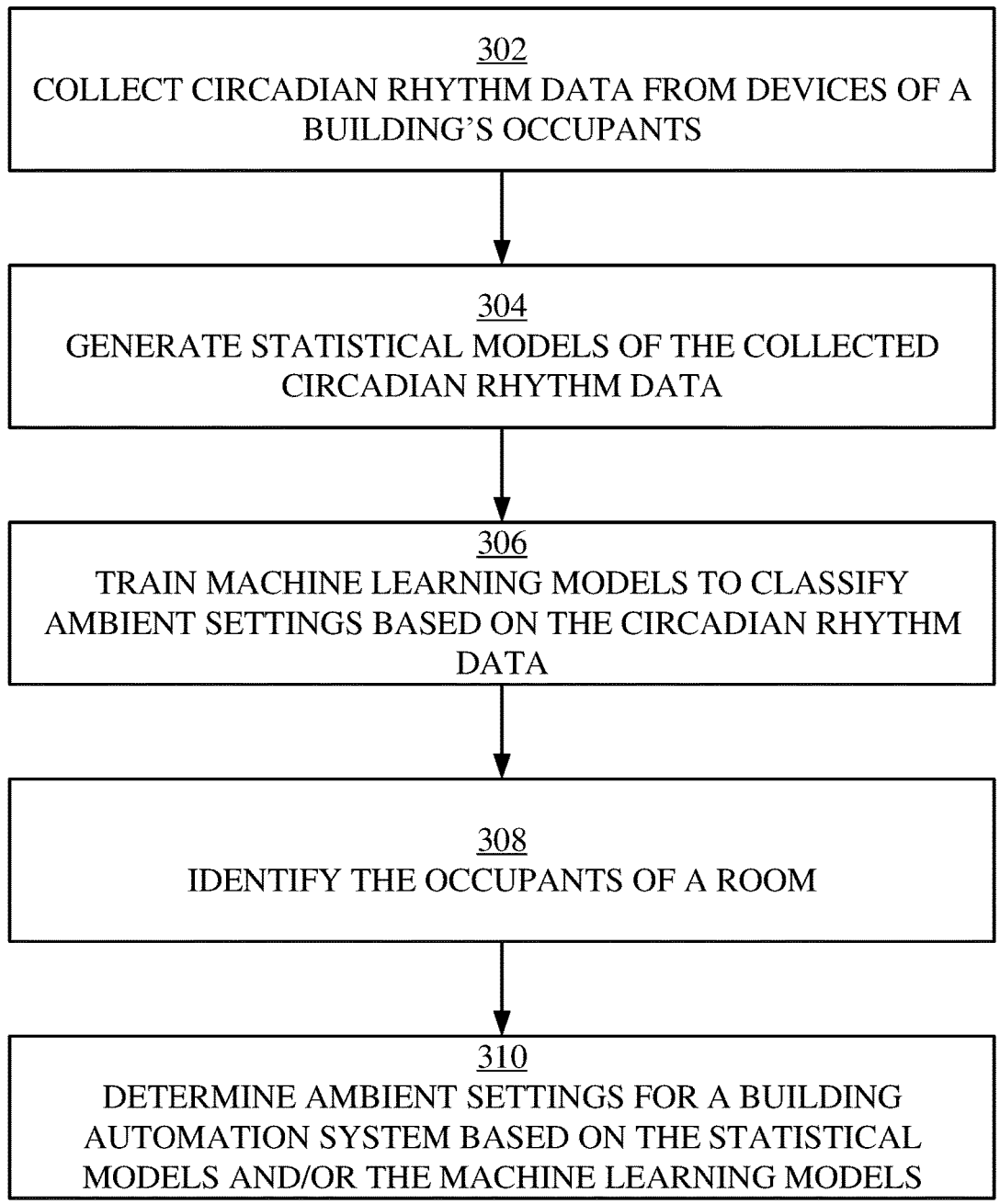
FIG. 3 is an example process flow diagram of a method for determining ambient settings, in accordance with some embodiments of the present disclosure.

FIG. 3 is a block diagram of an example process flow diagram of a method 300 for determining ambient controls, in accordance with some embodiments of the present disclosure. A circadian rhythm building automation engine, such as the circadian rhythm building automation engine 108, may perform the method 300.

At operation 302, the circadian rhythm building automation engine 108 can collect circadian rhythm data from devices of a building's occupants. The devices can include circadian rhythm data generating devices, such as the circadian rhythm data generating devices 104 described with respect to FIG. 1.

At operation 304, the circadian rhythm building automation engine 108 can generate statistical models of the collected circadian rhythm data. The statistical models can represent forecast of circadian rhythm data for the occupants wearing and/or carrying the circadian rhythm data generating devices 104.

At operation 306, the circadian rhythm building automation engine 108 can train machine learning models to classify ambient settings based on the collected circadian rhythm data. Training can involve training machine learning models to determine an ambient classification based on circadian rhythm data for an occupant. According to some embodiments of the present disclosure, the circadian rhythm building automation engine 108 can train a different model for each ambient system.

At operation 308, the circadian rhythm building automation engine 108 can identify the occupants of a room. The room may be located in a building having a building automation system, such as the building automation system 106. The occupants may be identified based on information provided by the circadian rhythm data generating devices 104.

At operation 310, the circadian rhythm building automation engine 108 can determine ambient settings for the building automation system 106 based on the statistical models and/or the machine learning models. If the room has more than one occupant, the ambient settings may be determined based on a trade-off between the corresponding ambient settings for each of the identified occupants.

According to some embodiments of the present disclosure, the circadian rhythm building automation engine 108 can alternatively identify another room (or portion of a room) having the determined ambient settings. Accordingly, the circadian rhythm building automation engine 108 can provide a notification to one or more of the occupants that indicates the identified room (or portion thereof). The notification can be a text message to a smartphone of the occupant, an email to a portable computing device of the occupant, and audio message from a smart speaker or smart watch, and the like.

Figure 4:
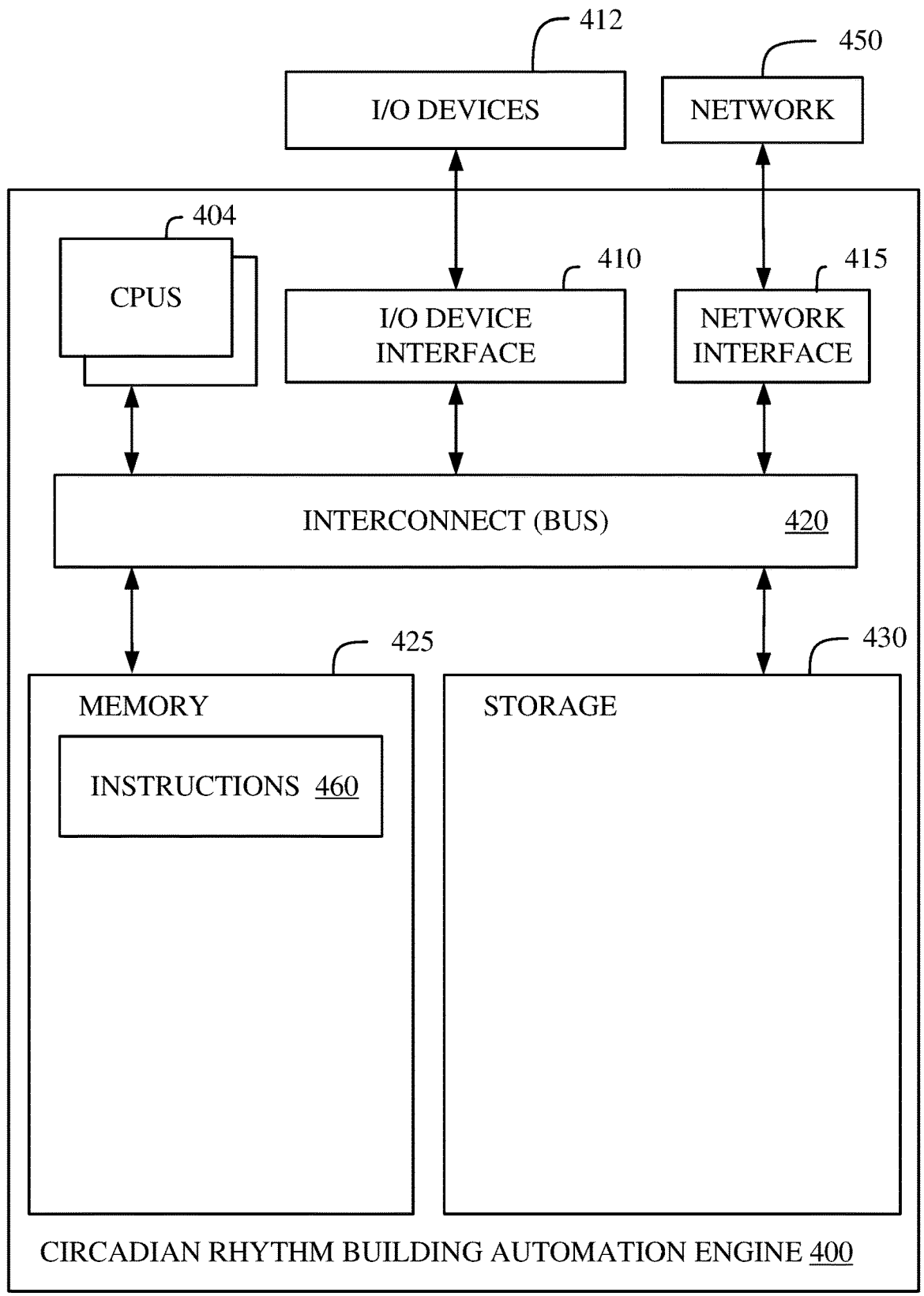
FIG. 4 is a block diagram of an example building automation system, in accordance with some embodiments of the present disclosure.

FIG. 4 is a block diagram of an example circadian rhythm building automation engine 400, in accordance with some embodiments of the present disclosure. In various embodiments, the circadian rhythm building automation engine 400 is similar to the circadian rhythm building automation engine 108 and can perform the method described in FIG. 3 and/or the functionality discussed in FIGS. 1-2. In some embodiments, the circadian rhythm building automation engine 400 provides instructions for the aforementioned methods and/or functionalities to a client machine such that the client machine executes the method, or a portion of the method, based on the instructions provided by the circadian rhythm building automation engine 400. In some embodiments, the circadian rhythm building automation engine 400 comprises software executing on hardware incorporated into a plurality of devices.

The circadian rhythm building automation engine 400 includes a memory 425, storage 430, an interconnect (e.g., BUS) 420, one or more CPUs 405 (also referred to as processors 405 herein), an I/O device interface 410, I/O devices 412, and a network interface 415.

Each CPU 405 retrieves and executes programming instructions stored in the memory 425 or the storage 430. The interconnect 420 is used to move data, such as programming instructions, between the CPUs 405, I/O device interface 410, storage 430, network interface 415, and memory 425. The interconnect 420 can be implemented using one or more busses. The CPUs 405 can be a single CPU, multiple CPUs, or a single CPU having multiple processing cores in various embodiments. In some embodiments, a CPU 405 can be a digital signal processor (DSP). In some embodiments, CPU 405 includes one or more 3D integrated circuits (3DICs) (e.g., 3D wafer-level packaging (3DWLP), 3D interposer based integration, 3D stacked ICs (3D-SICs), monolithic 3D ICs, 3D heterogeneous integration, 3D system in package (3DSiP), and/or package on package (PoP) CPU configurations). Memory 425 is generally included to be representative of a random access memory (e.g., static random access memory (SRAM), dynamic random access memory (DRAM), or Flash). The storage 430 is generally included to be representative of a non-volatile memory, such as a hard disk drive, solid state device (SSD), removable memory cards, optical storage, and/or flash memory devices. Additionally, the storage 430 can include storage area-network (SAN) devices, the cloud, or other devices connected to the circadian rhythm building automation engine 400 via the I/O device interface 410 or to a network 450 via the network interface 415.

In some embodiments, the memory 425 stores instructions 460. However, in various embodiments, the instructions 460 are stored partially in memory 425 and partially in storage 430, or they are stored entirely in memory 425 or entirely in storage 430, or they are accessed over a network 450 via the network interface 415.

Instructions 460 can be processor-executable instructions for performing any portion of, or all, any of the method described in FIG. 3 and/or the functionality discussed in FIGS. 1-2.

In various embodiments, the I/O devices 412 include an interface capable of presenting information and receiving input. For example, I/O devices 412 can present information to a listener interacting with circadian rhythm building automation engine 400 and receive input from the listener.

The circadian rhythm building automation engine 400 is connected to the network 450 via the network interface 415. Network 450 can comprise a physical, wireless, cellular, or different network.

In some embodiments, the circadian rhythm building automation engine 400 can be a multi-user mainframe computer system, a single-user system, or a server computer or similar device that has little or no direct user interface but receives requests from other computer systems (clients). Further, in some embodiments, the circadian rhythm building automation engine 400 can be implemented as a desktop computer, portable computer, laptop or notebook computer, tablet computer, pocket computer, telephone, smart phone, network switches or routers, or any other appropriate type of electronic device.

It is noted that FIG. 4 is intended to depict the representative major components of an exemplary circadian rhythm building automation engine 400. In some embodiments, however, individual components can have greater or lesser complexity than as represented in FIG. 4, components other than or in addition to those shown in FIG. 4 can be present, and the number, type, and configuration of such components can vary.

Although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third-party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third-party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
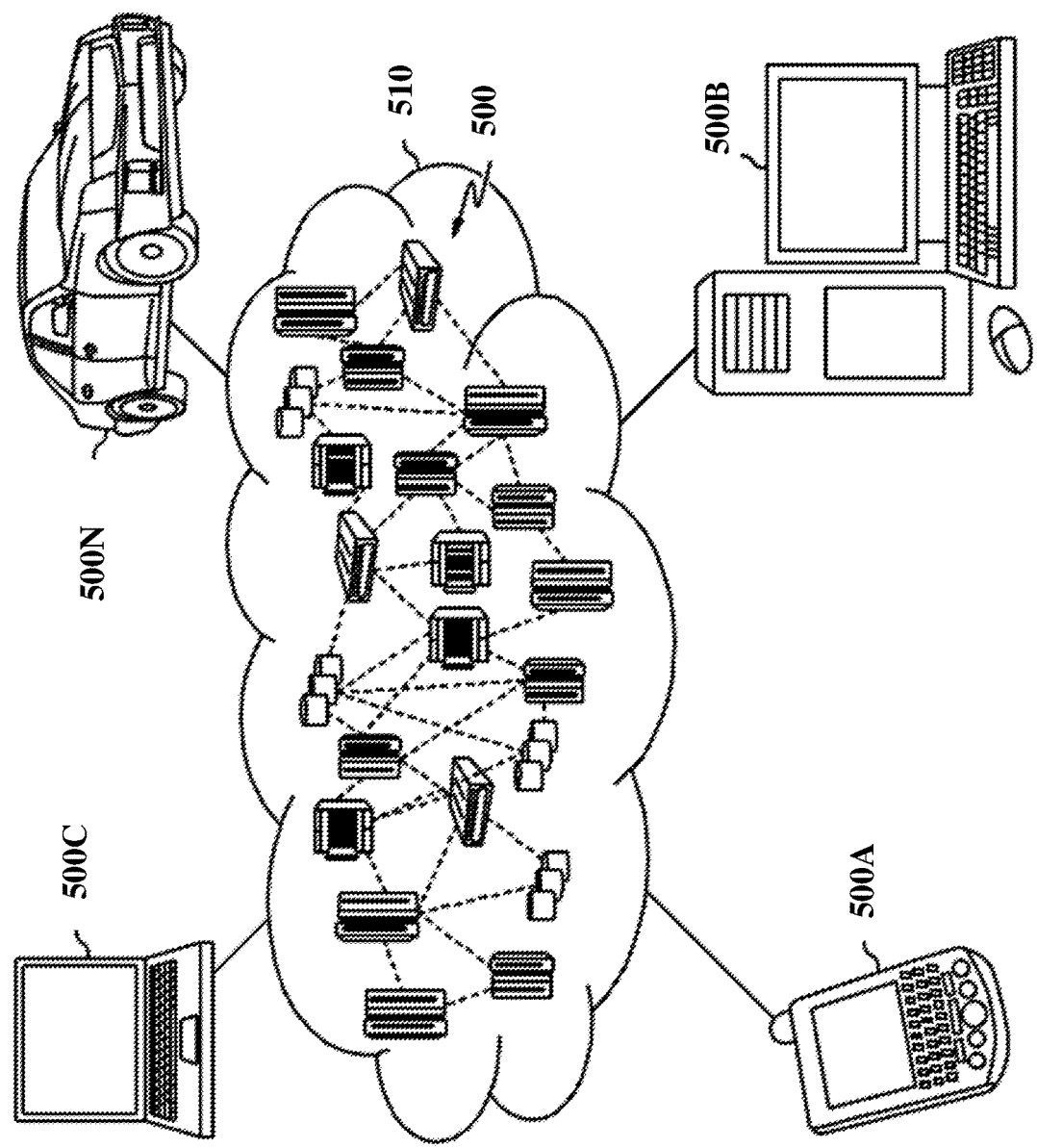
FIG. 5 is a cloud computing environment, in accordance with some embodiments of the present disclosure.

FIG. 5 is a cloud computing environment 510, according to some embodiments of the present disclosure. As shown, cloud computing environment 510 includes one or more cloud computing nodes 500. The cloud computing nodes 500 can perform the method described in FIG. 3 and/or the functionality discussed in FIGS. 1-2. Additionally, cloud computing nodes 500 can communicate with local computing devices used by cloud consumers, such as, for example, personal digital assistant (PDA) or cellular telephone 500A, desktop computer 500B, laptop computer 500C, and/or automobile computer system 500N. Further, the cloud computing nodes 500 can communicate with one another. The cloud computing nodes 500 can also be grouped (not shown) physically or virtually, in one or more networks, such as Private, Community, Public, or Hybrid clouds as described hereinabove, or a combination thereof. This allows cloud computing environment 510 to offer infrastructure, platforms and/or software as services for which a cloud consumer does not need to maintain resources on a local computing device. It is understood that the types of computing devices 500A-N shown in FIG. 5 are intended to be illustrative only and that computing nodes 500 and cloud computing environment 510 can communicate with any type of computerized device over any type of network and/or network addressable connection (e.g., using a web browser).

Figure 6:
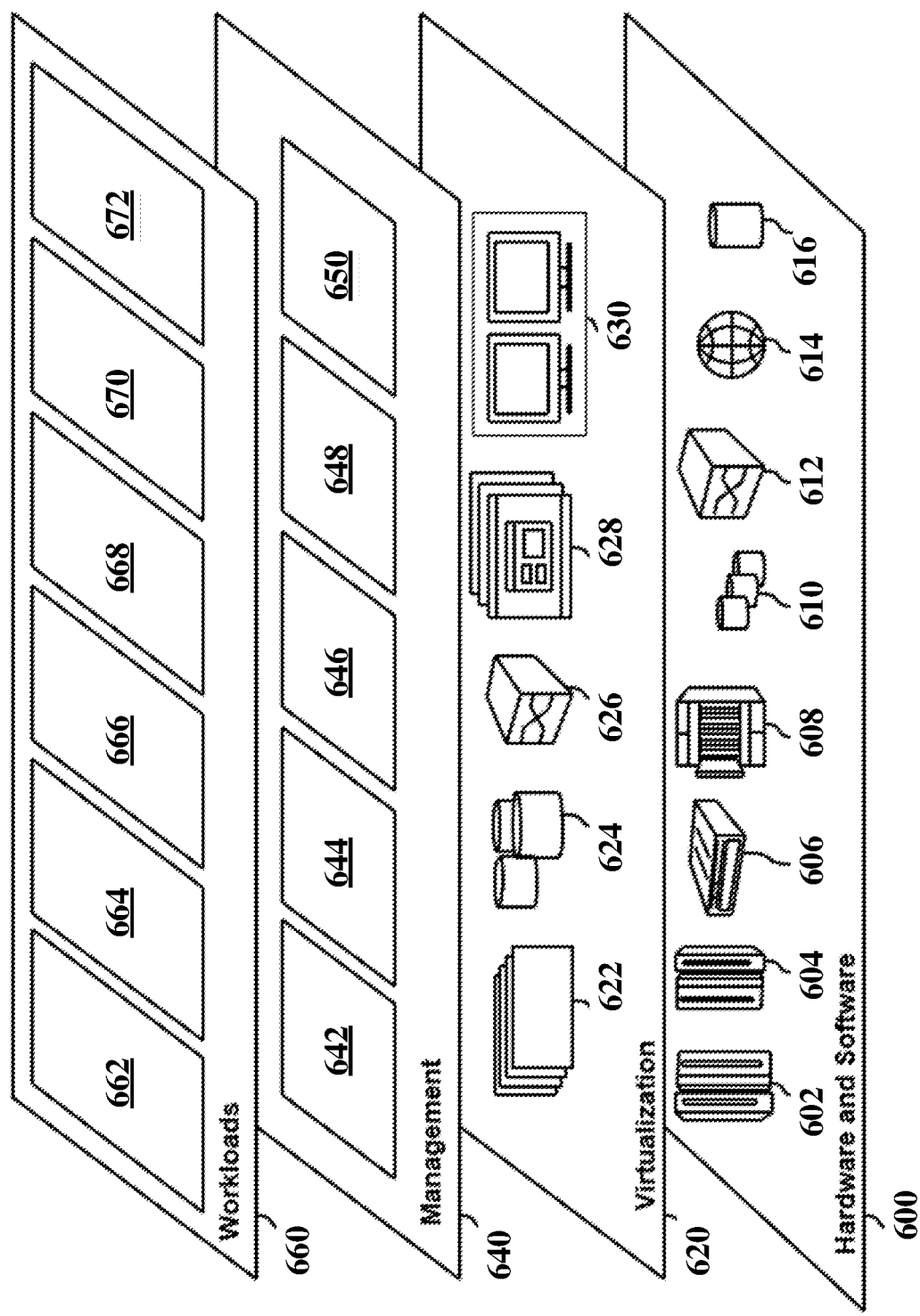
FIG. 6 is a set of functional abstraction model layers provided by the cloud computing environment, in accordance with some embodiments of the present disclosure.

FIG. 6 is a set of functional abstraction model layers provided by cloud computing environment 510 (FIG. 5), according to some embodiments of the present disclosure. It should be understood in advance that the components, layers, and functions shown in FIG. 6 are intended to be illustrative only and embodiments of the disclosure are not limited thereto. As depicted below, the following layers and corresponding functions are provided.

Hardware and software layer 600 includes hardware and software components. Examples of hardware components include: mainframes 602; RISC (Reduced Instruction Set Computer) architecture based servers 604; servers 606; blade servers 608; storage devices 610; and networks and networking components 612. In some embodiments, software components include network application server software 614 and database software 616.

Virtualization layer 620 provides an abstraction layer from which the following examples of virtual entities can be provided: virtual servers 622; virtual storage 624; virtual networks 626, including virtual private networks; virtual applications and operating systems 628; and virtual clients 630.

In one example, management layer 640 can provide the functions described below. Resource provisioning 642 provides dynamic procurement of computing resources and other resources that are utilized to perform tasks within the cloud computing environment. Metering and Pricing 644 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 646 provides access to the cloud computing environment for consumers and system administrators. Service level management 648 provides cloud computing resource allocation and management such that required service levels are met. Service level management 648 can allocate suitable processing power and memory to process static sensor data. Service Level Agreement (SLA) planning and fulfillment 650 provide pre-arrangement for, and procurement of, cloud computing resources for which a future requirement is anticipated in accordance with an SLA.

Workloads layer 660 provides examples of functionality for which the cloud computing environment can be utilized. Examples of workloads and functions which can be provided from this layer include: mapping and navigation 662; software development and lifecycle management 664; virtual classroom education delivery 666; data analytics processing 668; transaction processing 670; and circadian rhythm building automation engine 672.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, Java, Python or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method, comprising:
generating a plurality of forecast circadian rhythms based on a plurality of circadian rhythm data generated by a corresponding plurality of mobile computing devices of a plurality of occupants of a building, wherein the building has a building automation system;
training a machine learning model for the building automation system to perform an ambient setting classification based on historical circadian rhythm data for the plurality of occupants of the building;
identifying a plurality of room occupants of a room disposed within the building;
determining a plurality of ambient settings for an ambient system operated by the building automation system by performing the ambient setting classification for the identified room occupants;
determining a trade-off ambient setting based on the plurality of ambient settings by determining an average of the plurality of ambient settings; and
controlling the ambient system for the room based on the determined trade-off ambient setting.

2. The method of claim 1, further comprising collecting the circadian rhythm data from the mobile computing devices.

3. The method of claim 1, further comprising training a plurality of different machine learning models corresponding to a plurality of ambient systems operated by the building automation system.

4. The method of claim 1, further comprising identifying an ambient room having an ambient condition corresponding to the trade-off ambient setting.

5. The method of claim 4, further comprising providing a notification to one of the room occupants indicating the identified ambient room.

6. A computer program product comprising program instructions stored on a computer readable storage medium, the program instructions executable by a processor to cause the processor to perform a method comprising:
generating a plurality of forecast circadian rhythms based on a plurality of circadian rhythm data generated by a corresponding plurality of mobile computing devices of a plurality of occupants of a building, wherein the building has a building automation system;
training a machine learning model for the building automation system to perform an ambient setting classification based on historical circadian rhythm data for the plurality of occupants of the building;
identifying a plurality of room occupants of a room disposed within the building;
determining a plurality of ambient settings for an ambient system operated by the building automation system by performing the ambient setting classification for the identified room occupants;
determining a trade-off ambient setting based on the plurality of ambient settings by determining an average of the plurality of ambient settings; and controlling the ambient system for the room based on the determined trade-off ambient setting.

7. The computer program product of claim 6, the method further comprising collecting the circadian rhythm data from the mobile computing devices.

8. The computer program product of claim 6, the method further comprising training a plurality of different machine learning models corresponding to a plurality of ambient systems operated by the building automation system.

9. The computer program product of claim 6, the method further comprising identifying an ambient room having an ambient condition corresponding to the trade-off ambient setting.

10. The computer program product of claim 9, the method further comprising providing a notification to one of the room occupants indicating the identified ambient room.

11. A system comprising:
a computer processing circuit; and
a computer-readable storage medium storing instructions, which, when executed by the computer processing circuit, are configured to cause the computer processing circuit to perform a method comprising:
generating a plurality of forecast circadian rhythms based on a plurality of circadian rhythm data generated by a corresponding plurality of mobile computing devices of a plurality of occupants of a building, wherein the building has a building automation system;
training a machine learning model for the building automation system to perform an ambient setting classification based on historical circadian rhythm data for the plurality of occupants of the building;
identifying a plurality of room occupants of a room disposed within the building;
determining a plurality of ambient settings for an ambient system operated by the building automation system by performing the ambient setting classification for the identified room occupants;
determining a trade-off ambient setting based on the plurality of ambient settings by determining an average of the plurality of ambient settings; and
controlling the ambient system for the room based on the determined trade-off ambient setting.

12. The system of claim 11, the method further comprising training a plurality of different machine learning models corresponding to a plurality of ambient systems operated by the building automation system.

13. The system of claim 11, the method further comprising identifying an ambient room having an ambient condition corresponding to the trade-off ambient setting.

14. The system of claim 13, the method further comprising providing a notification to one of the room occupants indicating the identified ambient room.

* * * * *